United States Patent
Beard et al.

(10) Patent No.: US 8,306,779 B2
(45) Date of Patent: Nov. 6, 2012

(54) DETECTABLE DEFECT SIZE AND PROBABILITY-OF-DETECTION

(75) Inventors: Shawn J. Beard, Livermore, CA (US); Fu-Kuo Chang, Stanford, CA (US)

(73) Assignee: Acellent Technologies, Inc., Sunnyvale, CA (US)

( * ) Notice: Subject to any disclaimer, the term of this patent is extended or adjusted under 35 U.S.C. 154(b) by 775 days.

(21) Appl. No.: 12/039,582

(22) Filed: Feb. 28, 2008

(65) Prior Publication Data
US 2008/0255803 A1    Oct. 16, 2008

Related U.S. Application Data

(60) Provisional application No. 60/912,112, filed on Apr. 16, 2007.

(51) Int. Cl.
*G06F 17/18* (2006.01)
*G06F 11/00* (2006.01)

(52) U.S. Cl. ......... 702/181; 702/182; 702/183; 702/188

(58) Field of Classification Search .......... 702/121–123, 702/181–190
See application file for complete search history.

(56) References Cited

U.S. PATENT DOCUMENTS
2006/0079747 A1 *   4/2006   Beard et al. ................. 600/407
* cited by examiner

*Primary Examiner* — Phuong Huynh
(74) *Attorney, Agent, or Firm* — Innovation Counsel LLP

(57) ABSTRACT

Predicting the probability of detection of major and minor defects in a structure includes simulating a plurality of N defects at random locations in a region specified by an array of transducers. Defect size is incremented until it intersects one path between two transducers. The defect size is again incremented until it intersects two or more adjacent paths between pairs of transducers. The number of major defects up to a selected size is determined by the total number of single path intersections by defects up to the selected size. The number of minor defects up to a selected size is determined on the basis of the total number of defects intersecting two or more paths up to the selected size. The probability of detection up to a selected size is the cumulative number of major or minor defects up to the selected size normalizing by N.

19 Claims, 5 Drawing Sheets

DETECTABLE DEFECT SIZE AND PROBABILITY-OF-DETECTION

CROSS-REFERENCE TO RELATED APPLICATION

This application claims the benefit of U.S. Provisional Patent Application Ser. No. 60/912,112, entitled "STRUCTURAL HEALTH MONITORING SYSTEM AND METHODS FOR USE," filed on Apr. 16, 2007, which is hereby incorporated by reference in its entirety.

TECHNICAL FIELD

This invention relates generally to transducer arrays for structural health monitoring. More specifically, this invention relates to the determining the detectable defect size for a given transducer arrangement and creating probability of detection curves.

BACKGROUND

Probability of detection (POD) is being introduced as a standard measurement for quantifying the reliability and robustness of built-in structural health monitoring systems. It has become common practice to quantify the reliability of flaw detection in terms of the probability of detection (POD).

POD tries to assess a minimum flaw size that will be reliably detected by a non-destructive testing (NDT) technique. This is best done by plotting the accumulation of flaws detected against the flaw size of all the flaws "detected," where "detected" may mean producing a signal response that exceeds some threshold. Ideally all flaws over some critical size will be detected and smaller flaws are not "detected". The tool most commonly used for POD description is the POD curve. The POD curve is useful in providing a reference method of quantifying the performance capability of an NDT procedure.

However, traditional POD curves are typically generated for single points and are obtained through extensive testing, which is not practical for every new structure and transducer array configuration. Structural health monitoring, e.g., the detection and location of defect damage in a structure, using an array of transducers, where the transducers may serve both as actuators and sensors, may require a modified or different approach. Experimental measurement may be expensive and yield answers based on poor statistics which may be caused, for example, by noise in the detection system, or a lack of sufficient test data; therefore attention has recently turned to modeling. To overcome this difficulty it is desirable to have a method to predict the POD for the entire structure, or any sub-region thereof, using merely the transducer coordinates, the operating actuator-sensor paths and the logic of a given damage detection process.

SUMMARY

In one embodiment of the invention, a method is provided to predict the probability of detecting a defect in a structure based on the size and location of the defect. The defect is considered as a circular object at a randomly selected coordinate location. An array of transducers may be attached to the structure, and the coordinate locations of the individual transducers are known. Paths between selected transducers are established representing transmission of signals from a first transducer to a second transducer. If the selected path intersects the object of a given size, the damage is classified as severe. If two adjacent selected paths intersect the object, the damage is classified as minor.

In an embodiment of the invention a transducer array may be embedded within a flexible layer, which can then be attached to a structure and employed to monitor its structural health. The transducer array employs transducers, capable of acting as both passive sensors and active actuators. For example, the transducers may be piezoelectric ceramic or polymer transducers. Piezoelectric transducers are capable of both generating and detecting ultrasonic waves that propagate along the surface, or through the bulk of a structure. Transmission of such signals between two or more such transducers (i.e., pitch-catch, or bistatic), or reflection of such a signal from a discontinuity, such as a crack, for example, back to the same transducer (i.e., backscatter, or monostatic) may be used to detect damage in the structure. By acquiring a plurality of signals from combinations of paths across the transducer array, a determination of the size and location of such structural defects can be made.

These transducers are controlled by local electronics that may also be embedded within or attached to the structure in the same or a manner similar to that used for the array of transducers.

After a transducer layout has been defined and the operating actuator-sensor paths have been determined, one can generate POD curves. The computations use the geometry of the transducer configuration and the selected actuator-sensor paths, along with the logic of a given damage detection process, to generate the POD curves for the entire structure, or a sub-region thereof.

These and other features and advantages of the present invention will be more readily apparent from the detailed description of the preferred embodiments set forth below taken in conjunction with the accompanying drawings.

BRIEF DESCRIPTION OF THE FIGURES

Like element numbers in different figures represent the same or similar elements.

DETAILED DESCRIPTION

Figure 1:
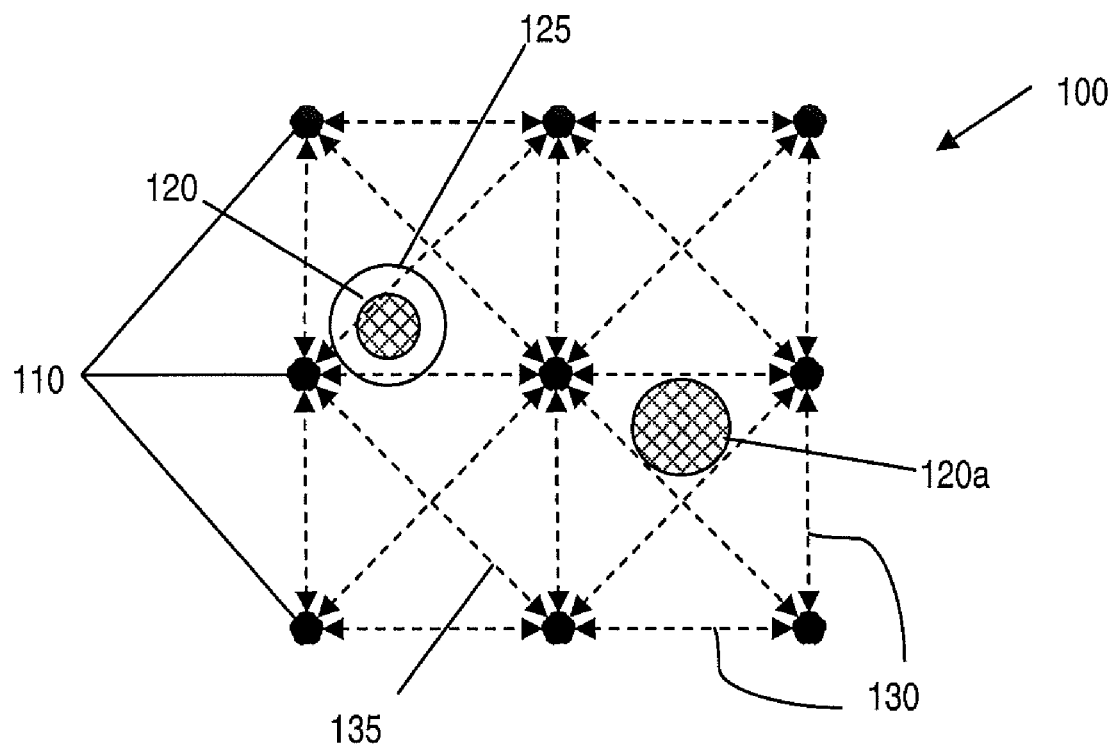
FIG. 1 illustrates a transducer array for use with the present disclosure according to one embodiment.

FIG. 1 shows a representative array 100 of transducers 110 that function as both actuators and sensors for detecting damage defects in a structure, in accordance with an embodiment of the disclosure. As will be described below, the defects may be classified as major (or severe) defects 120 or minor defects 125. Paths 130 and 135, indicated by dotted line arrows, may be paths designated to transmit elastic wave signals, for example, between a transmitting transducer and a sensing transducer. Here, the paths shown are horizontal or vertical, which may be characterized as "nearest neighbor" paths 130, and diagonal, which may be characterized as "next-nearest" neighbor paths 135. Additional paths may be specified, for example, which connect transducers located farther apart. This may be advantageous when a transducer itself may be defective, or is not adequately bonded to the structure being inspected for defects.

A defect may be located such that it intersects a direct path between two transducers, or it may be located such that it does not intersect a direct path. Signals transmitted by an actuated transducer, however, may radiate, for example, in a circular pattern, i.e., in all directions, so that a major defect 120 that is not in-line may scatter the signal and be detected at a sensor. In this case, the time-of-arrival will be delayed because the path followed by the detected scattered signal is longer than that of a directly transmitted signal.

Three main categories of conditions may occur: (1) there is no defect detected in signals transmitted between two transducers, (2) there is a major (severe) defect 120, and (3) there is a minor defect 125. In addition, where a defect (minor or major) may occur, it may be in a location directly in-line between two transducers, or it may be offset from the direct path, as indicated above.

FIGS. 2A-2E illustrate various scenarios of transmission of an elastic wave signal as a pulse between a transmitting transducer and a sensing transducer, such as shown in FIG. 1. It is assumed in this example, that there are no cut-outs, i.e., regions of a structure for which there is no direct transmission path between transducers.

Figure 2A:
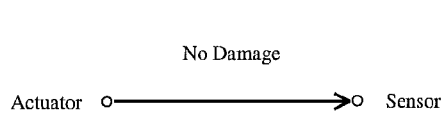
FIG. 2A illustrates a baseline signal received when no defect is detected, according to an embodiment of the disclosure.
Figure 2A:
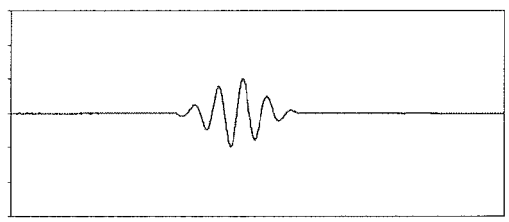

FIG. 2A illustrates a case where there is no defect, showing the elastic wave signal that may be received at the receiving sensor transducer. The received signal may be characterized as a baseline signal. The time-of arrival is determined by the distance separating the two transducers and the velocity of elastic wave propagation within the structure.

The determination of what constitutes a major or minor defect 120 or 125, respectively, may depend on selection of a threshold signal level relative to a baseline. Such measurements are subject in practice to test conditions and user consistency, and are dependent on actual test data and procedures. Additionally, it is noted that the threshold signal amplitude distinguishing "major" from "minor" may be arbitrary. Therefore, a definition of major and minor defect is developed in this disclosure, independent of the relative signal amplitudes detected corresponding to the type of defect, for purposes of prediction of detectability. For the benefit of context, however, a discussion of the types of results that may be expected in actual experimental measurements is presented below.

Figure 2B:
FIG. 2B illustrates a signal detected with a minor defect in-line with the transmission path between two transducers, according to an embodiment of the disclosure.
Figure 2B:
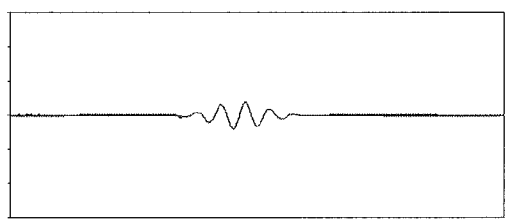
Figure 2C:
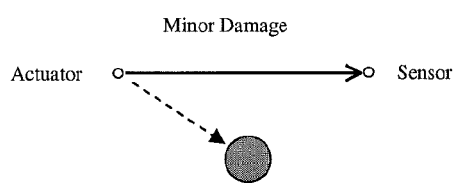
FIG. 2C illustrates a signal detected with a minor defect not located in-line with the transmission path between two transducers, according to an embodiment of the disclosure.
Figure 2C:
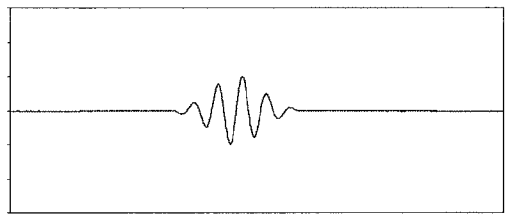

FIG. 2B illustrates the case where a minor defect 125 lies directly in the path of a signal transmitted between two transducers. The detected signal may be attenuated relative to a corresponding baseline signal, but will have the same time-of-arrival. FIG. 2C illustrates the case where a minor defect occurs, but does not lie on a direct path between two transducers. The defect 125 is weak enough that no detectable wave scattered from the defect is detected at the sensing transducer. It is noted that a minor defect centered at the same location, but of a larger size, may then be detected as in the case shown in FIG. 2B, when the diameter of the defect is large enough to intersect a direct path.

Figure 2D:
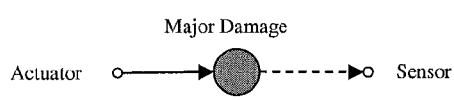
FIG. 2D illustrates a signal detected with a major defect located in-line with the transmission path between two transducers, according to an embodiment of the disclosure.
Figure 2D:
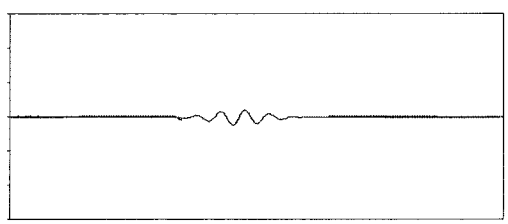

FIG. 2D illustrates the case where a major defect 120 lies directly on a path between two transducers. The elastic wave signal may then be strongly attenuated relative to a baseline signal, or it may not be detected at all. When the signal is weakly detected, the time-of-arrival may be substantially the same as in the cases shown in FIGS. 2A-2C.

Figure 2E:
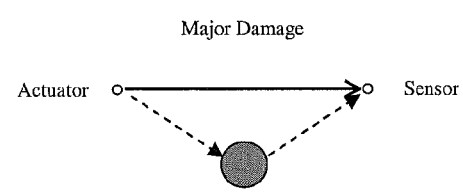
FIG. 2E illustrates a signal detected with a major defect not located in-line with the transmission path between two transducers, according to an embodiment of the disclosure.
Figure 2E:
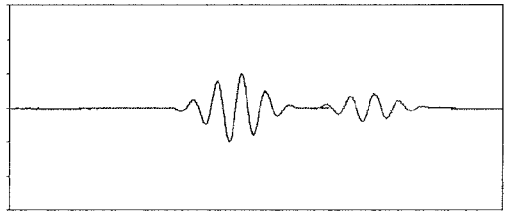

FIG. 2E illustrates the case where a major defect 120 does not lie on the direct path between two transducers. However, the defect is severe enough to strongly scatter a wave transmitted by the actuating transducer and may be detected by the sensing transducer. In this case, two pulses may be detected: the direct in-line pulse, which is substantially the same amplitude as the baseline signal pulse generated by the actuator, and a second pulse, corresponding to the elastic wave scattered from the defect. Because the path from the actuating transducer to the sensing transducer by way of the defect is longer, the time-of-arrival of the scattered pulse signal is delayed relative to the direct path pulse.

With the foregoing description serving as an exemplary configuration of transducers 110 forming an array 100 affixed to a structure (not shown) for structural health monitoring, a method may be obtained that predicts the probability of detection (POD) of defects in the structure. Defects may be characterized as having a point coordinate location and a size defined by a radius. Thus, defects may be considered as circular (or spherical) "objects" defined by a radius. While a defect may be considered "large" or "small" according to some criteria, in this disclosure, a defect is considered "minor" or "major" according to the characteristics of the paths 130 or 135 intersected, regardless of size.

Conventional POD analysis, which is based on extensive testing and accumulation of data from individual defects, may typically result in producing a set of curves which depict the POD (expressed as a percentage) versus the size of the defect damage (which may be expressed, for example, as the radius or diameter), where each curve corresponds to a confidence level (e.g., 50%, 90%, 99%, etc) of detection of defects. Thus, a lower (e.g., 50%) confidence level curve will rise toward a 100% POD with increasing defect size more quickly than a higher (e.g., 90%) confidence level curve. As the size of the defect increases, eventually the defect may be substantially equal or greater than the distance between two transducers, at which point there is substantially a 100% probability of detection, regardless of the confidence level, since it is guaranteed that one or more transmission paths 130 or 135 are intersected by the defect. Confidence level may be a function of the nature of the transducer, detection thresholds set by a detection system, and in the case of manual measurements of individual defects, user skill, reliability and consistency.

According to embodiments of the disclosure, however, where an array 100 of transducers 110 are bonded, or affixed, to a structure for structural health monitoring, POD curves for structural monitoring where a plurality of defects may occur may be defined to specify the POD for major damage and for minor damage. Alternatively, various levels of damage may be defined, and a plurality of POD curves may be generated corresponding to each level of damage. For purposes of explanation, detection of two levels of defect are described, but the description is not intended to be limiting.

Figure 3:
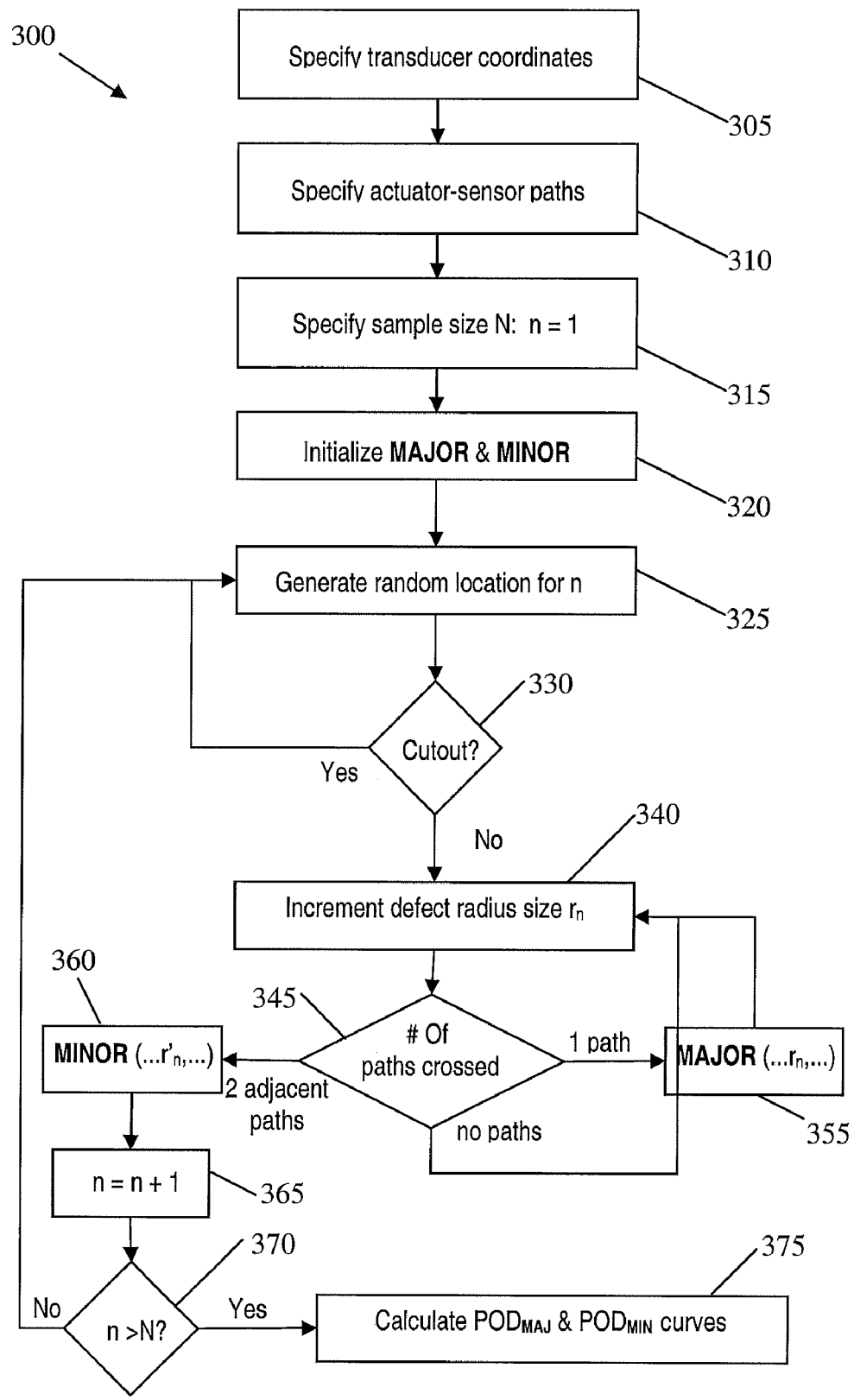
FIG. 3 is a flow diagram of the method of predicting the POD of major and minor damage, according to an embodiment of the disclosure.
Figure 4:
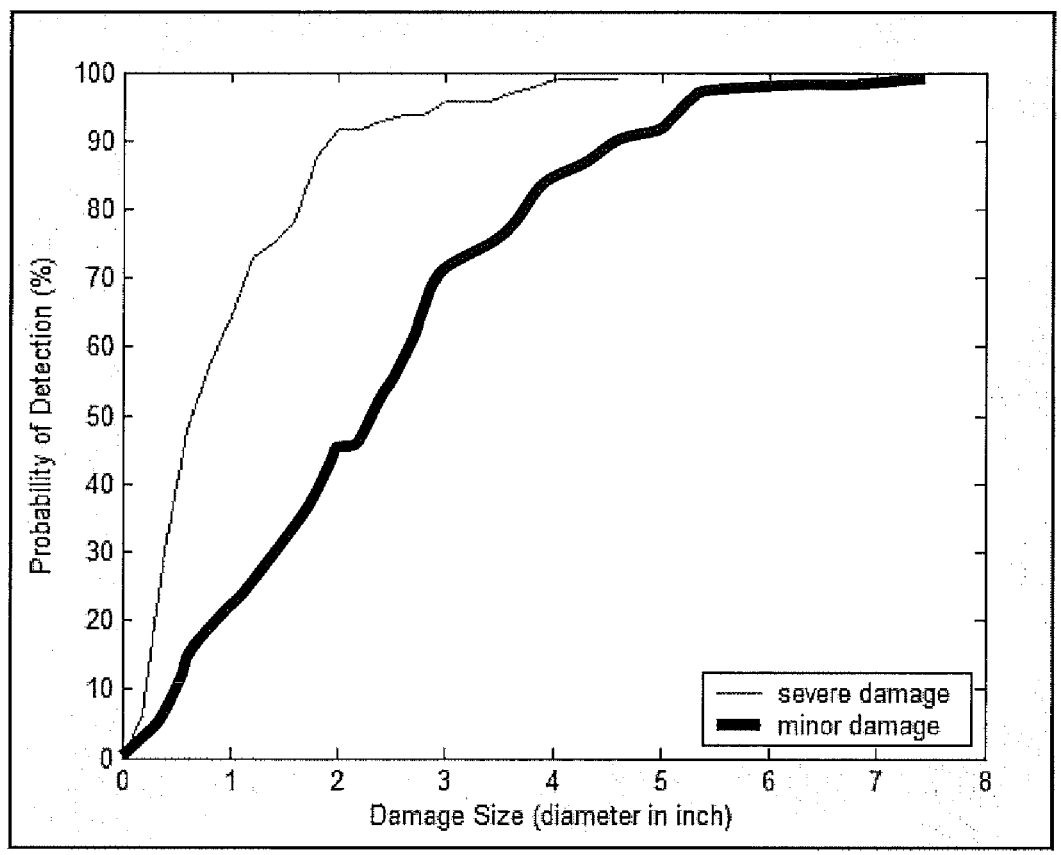
FIG. 4 is an exemplary graph illustrating the probability of detection of major and minor defects, according to an embodiment of the disclosure.

According to an embodiment of the method, FIG. 3 is a flow diagram of a method 300 for predicting the POD of major and minor damage as a function of damage size. With reference to FIG. 3, the following steps may be implemented to obtain a POD curve for major (severe) defect damages and for minor defect damages. The embodiment presented is a model for prediction classification of defects as major or minor determined according to their intersection with paths in the transducer array. Therefore, the classification decision process is based on the (random) location of the defect and its size, of radius r, relative to predetermined transducer paths 130 and 135 of array 100.

A spatial model of a structure (not shown) and a representation of array 100 may first be specified (block 305), such as by creating a file comprising the coordinates of the transducers 110 located on the structure, and indexing each transducer 110 appropriately for identification. Paths connecting transducers 110 may be specified (block 310) for later determination of whether a defect intersects a path or not. For example, path 130 (as in FIG. 1) is a "nearest neighbor path," which in the example array 100, being arranged in a substantially square pattern, are found to be horizontal or vertical and are termed paths 130. Diagonal paths, as shown in FIG. 1, are therefore longer, and would be "next-nearest neighbor" paths 135. If, alternatively, for example, array 110 is comprised of a non-square rectangular arrangement of transducers 110, path 130 would correspond to the shorter side of the rectangle, path 135 would correspond to the longer side, and a diagonal path would correspond to a "second nearest neighbor" path (not shown).

The spatial model of the structure may contain cut-outs, such as, for example, a window in an airplane fuselage. This information may be used to exclude paths that would intersect the cut-out.

A sample size N corresponding to the total number of defects to be found in the region specified by array 100 may be specified and a loop counter n initialized to n=1 (block 315). n will increment by 1 up to N. Two vectors may be defined, i.e., MAJOR and MINOR (in block 320), where each vector has a dimension N. Each coordinate in the respective vectors has a value corresponding to a radius $r_n$ of defect n. Thus each vector may have the form $MAJOR(r_1, \ldots r_n, \ldots r_N)$ and $MINOR(r'_1, \ldots, r'_n, \ldots, r'_N)$. Initially, all coordinates of MAJOR and MINOR have zero (null) values, i.e., $(0, \ldots 0, \ldots, 0)$.

A random location is generated (block 325) defining a defect site corresponding to the current index value of n. Each location may be constrained to lie within the region defined by array 100. Thus, a total of up to N defects may ultimately be generated, i.e., N is the number of "simulated defects" chosen for purposes of determining representative POD curves for the array 100 and structure. The randomly chosen coordinates locating each defect may be stored in a separate table with corresponding index value. If a model of the structure that will be monitored by array 100 contains a cut-out, such as, for example, a window in an airplane fuselage, then a decision (block 330) may be made to generate another random location by returning to block 325.

If no cut-out exists at the current defect location, the defect with index n is then assigned a size characterized by a radius $r_n$ (block 340) that begins with dimension zero and is incremented in steps of a selected amount. Given the finite size of the defect, a test is made (decision block 345) to determine if the defect intersects any path as specified in block 310. If no paths are intersected, the defect radius is incremented in block 340 and the test repeated in decision block 345. Alternatively, if only one path is intersected, the defect in then identified as major, and the vector MAJOR is adjusted so the coordinate corresponding to the defect of location n has the value $r_n$, and the defect is identified as a major defect 120 of radius $r_n$.

If a defect of index n of a given radius intersects two paths defined by block 310, the defect is determined to be minor, and a similar procedure as described above is performed (block 360) to populate MINOR at the coordinate corresponding to defect with index n with a radius $r'_n$. Thus, the MINOR vector has the form $MINOR(r'_n, \ldots, r'_n, \ldots, r'_N)$. Note that the approach described in connection with blocks 345-360 defines major defects as intersecting a single sensor path 130, 135, and minor defects as intersecting two sensor paths 130, 135. This approach reflects the assumption that, often, defects take the shape of a generally central region having more severe damage, surrounded by a region having less severe damage. That is, defects often take the form of a central area of major defect, surrounded by an area of minor defect. However, it should also be noted, as above, that the invention encompasses any other useful definition of major and minor defects.

The following properties may be noted with respect to decision block 345. If defect n is found to intersect two paths immediately, without first intersecting one path, MAJOR is not updated to provide a defect size at the corresponding coordinate n, and remains a null value, i.e., $r_n=0$, while $r'_n$ has a finite value. Otherwise, defect location n may be the location of both a major defect 120 of radius $r_n$ and a minor defect of radius $r'_n$.

If a minor defect has been determined in block 345 and the vector MINOR updated in block 360, the defect radius increment loop is terminated and the location index n is incremented by 1 (block 365). An index decision block 370 determines whether n exceeds the value N. If not, the outer loop corresponding to index n is continued by returning to block 325 to generate another location for the next defect of updated index value n. The method repeats, as described above, determining the defect radius at which a defect location is, respectively, MAJOR and MINOR.

When index decision block 370 determines that n exceeds N, the random location generation loop that began at block 325 is terminated and a calculation (in block 375) is performed that provides the probability of detection curves $POD_{MAJ}(r)$ and $POD_{MIN}(r)$. Both curves may be presented in the same graph, or separately.

After the detectable damage sizes have been determined from all N locations, the POD curves can be generated using the following formulas:

$$POD_{MAJ}(r) = \frac{\text{Number\_of\_major\_defects\_with\_size} \leq r}{N} \quad (1)$$

and $$POD_{MIN}(r) = \frac{\text{Number\_of\_minor\_defects\_with\_size} \leq r}{N} \quad (2)$$

For a given value of r, the defect radius size, $POD_{MAJ}(r)$ is the cumulative number of major defects found up to and including defects of radius r, and similarly for $POD_{MIN}(r)$. Therefore, as defects (whether major or minor) of increasing size are considered, the probability of detecting a large enough defect must approach 100%. For example, considering a square array 100 as shown in FIG. 1, if the nearest neighbor spacing between transducers 110 is $\ell$, the radius of the largest defect that can be placed in array 100 without touching any paths must be less than $r=(\ell/2)$ $\tan(22.5°)=0.207\ell$. Thus, by the time a defect increases to about 21% of the transducer spacing, there is a probability of substantially 100% of detection.

In this manner, one of ordinary skill in the art will realize that embodiments of the invention allow for quick and easily automated determination of POD curves for the entire array 100 and structure it covers. That is, by generating a set of simulated defects at random locations within the array 100 and incrementing their sizes until they are detected by first one and then two sensor paths (corresponding to major and minor defects, respectively), the above described methods allow for automatic determination of detectable defect size at many different locations on the structure, allowing for estimation of "overall" POD curves by estimations such as equations (1) and (2).

One of ordinary skill in the art will also realize that the invention is not limited to the embodiments described. For example, while defects are simulated as circular or spherical, the methods of the invention can be employed in conjunction with simulated defects of any shape or geometry that can be characterized by a dimensionable feature (e.g., elliptical defects whose major and minor axes can be varied, cracks whose directions and lengths can be varied, etc.). The invention also contemplates selection of locations for simulated defects in any manner, including random selection (described above), pseudorandom selection, manual selection, or any other known approach.

Figure 5:
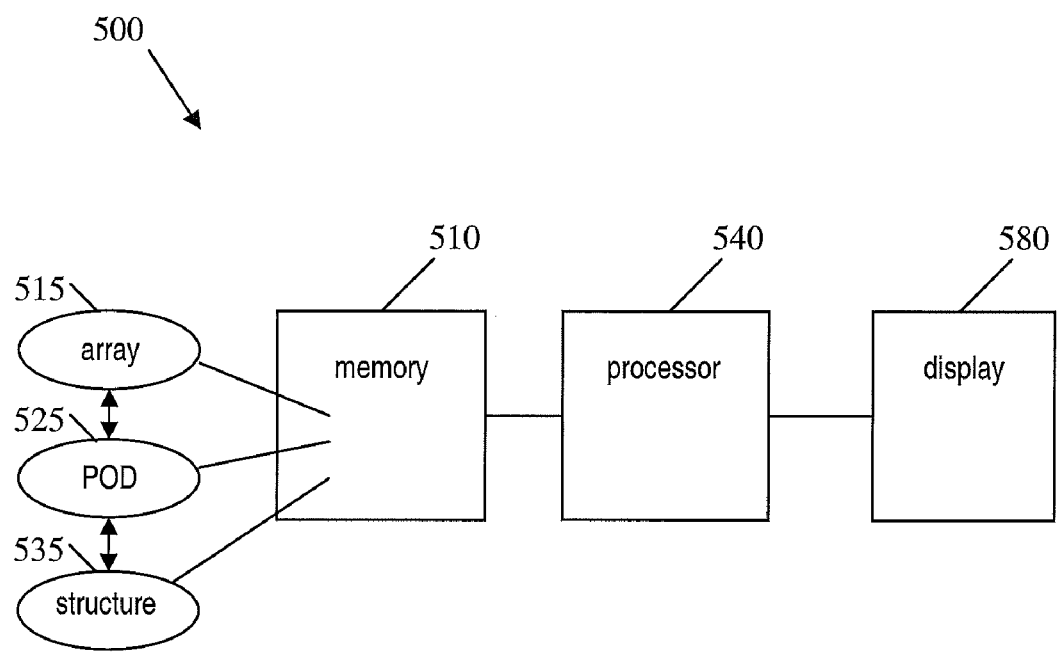
FIG. 5 illustrates a system for predicting the POD of major and minor damage defects, according to an embodiment of the disclosure.

A system 500 for predicting the POD of major and minor damage defects for structural health monitoring is shown in FIG. 5. System 500 comprises a memory 510 for storing an array file 515 of a spatial representation of a simulated array 100 of transducers 110, a structure file 535 of a spatial representation of a simulated structure, and a machine readable program 525 for calculating the probability of detection of major and minor defects in the structure based on the files 515 and 535 and the program 525. System 500 further comprises a processor for executing program 525 on the basis of files 515 and 535, and a display 580, which may be at least one of a printer or monitor capable of providing the POD curves 400.

Having thus described embodiments of the present disclosure, persons of ordinary skill in the art will recognize that changes may be made in form and detail without departing from the scope of the invention. Thus the invention is limited only by the following claims.

What is claimed is:

1. A computer-implemented method of predicting the probability of detection of major and minor defects in a structure, comprising:
  simulating a plurality of defects at locations in a region specified by a plurality of transducers formed in an array on the structure;
  in a digital computer or controller, incrementing a size of each defect until the incremented defect intersects one path between two of the transducers;
  in the digital computer or controller, incrementing the size of each defect until the incremented defect intersects two or more adjacent ones of the paths;
  for each size, determining in the digital computer or controller a number of major defects according to a number of the incremented defects intersecting one path;
  for each size, determining in the digital computer or controller a number of minor defects according to a number of the incremented defects intersecting two or more paths; and
  for each size, computing a probability of detection of major and/or minor defects by normalizing the number of major defects and/or minor defects for that size by the number of simulated defects, the probability of detection estimating a likelihood of detecting defects of that size.

2. The method of claim 1, further comprising defining a coordinate configuration of a plurality of transducers attached to the structure.

3. The method of claim 2, further comprising: providing a first characteristic dimension for a one of the defects;
  repeating the incrementing of the first characteristic dimension until a first path intersects the defect;
  once the first path intersects the defect, labeling the defect of the first characteristic dimension as major;
  incrementing the first characteristic dimension to a second characteristic dimension;
  repeating the incrementing of the second characteristic dimension until two or more adjacent paths intersect the defect; and
  once the two or more adjacent paths intersect the defect, identifying the defect of the second characteristic dimension as minor.

4. The method of claim 3, further comprising
  repeating the steps of claim 3 for all locations in the set of N samples;
  computing the probability of detection of major defects based on the labeling; and
  computing the probability of detection of minor defects based on the identifying.

5. The method of claim 1, further comprising:
  providing a table or graph of the probability of detection of major and/or minor defects as a function of defect size, wherein the probability of detection of major and/or minor defects as a function of defect size is the cumulative probabilities of detection for defects equal to or less than the selected size.

6. An apparatus for predicting the probability of detection of major and minor defects in a structure by a transducer array, comprising:
  a machine readable memory which is a non-transitory computer readable medium;
  a machine readable file stored in the memory and including computer readable data specifying coordinates of transducers and specifying the structure;
  a program stored in the memory, the program including computer instructions for causing a computer to simulate defects and to compute probabilities of detection from the simulated defects, the specified coordinates and the specified structure, the probabilities of detection estimating when defects are detectable by the array and whether each defect of the selected size is major or minor; and
  an output device for providing a probability of detection curve corresponding to the major or minor defect as a function of defect size.

7. The apparatus of claim 6, wherein the program is configured to generate of the simulated defects at random locations in a region specified by the array.

8. The apparatus of claim 7, wherein the program is adapted to specify paths between transducers in the array.

9. The apparatus of claim 8, wherein the program is configured to increment the size of the defect to a first size when it intersects a first path between two of the transducers, the defect then being identified as a major defect having the first size.

10. The apparatus of claim 8, wherein the program is configured to increment the size of the defect to a second size when it intersects at least a second adjacent path between two of the transducers, the defect then being identified as a minor defect having the second size.

11. The apparatus of claim 9, wherein the program is adapted to compute the total number of the major defects detected having all sizes up to the selected first size.

12. The apparatus of claim 10, wherein the program is adapted to compute the total number of the minor defects detected having all sizes up to the selected second size.

13. The apparatus of claim 11, wherein the program is adapted to compute the probability of detection of all the major defects up to a selected first size by normalizing the total number of major defects detected up to a selected first size by a number N.

14. The apparatus of claim 12, wherein the program is adapted to compute the probability of detection of all minor defects up to a selected second size by normalizing the total number of minor defects detected up to the selected second size by a number N.

15. The apparatus of claim 6, wherein the output device is at least one of a memory, printer, and monitor.

16. A computer-implemented method of determining probabilities of detection of defects in a structure, comprising:
in a non-transitory computer-readable memory, storing position information corresponding to positions of transducers coupled to a structure;
in the non-transitory computer-readable memory, storing path information corresponding to locations of sensor paths between the transducers; and
in a digital computer or controller, automatically determining probabilities of detection of defects in the structure from the stored position information and the stored path information, the probabilities of detection estimating likelihoods of detection of defects by the transducers.

17. The method of claim 16, wherein the automatically determining further comprises:
simulating defects in the structure;
determining sizes of the simulated defects when the simulated defects intersect ones of the sensor paths; and
determining the probabilities of detection according to the determined sizes and a number of the simulated defects.

18. The method of claim 17:
wherein the determining sizes further comprises determining, for each of the simulated defects, a first size at which the each simulated defect intersects one of the sensor paths according to the stored path information, and a second size at which the each simulated defect intersects two of the sensor paths according to the stored path information; and
wherein the determining the probabilities further comprises determining probabilities of detection of major defects from the first sizes relative to the number of the simulated defects, and determining probabilities of detection of minor defects from the second sizes relative to the number of the simulated defects.

19. The method of claim 17, wherein the simulating further comprises selecting locations of the simulated defects within the structure, and incrementing sizes of the simulated defects until the simulated defects intersect ones of the sensor paths.

* * * * *